United States Patent
Yada et al.

(10) Patent No.: US 7,041,850 B2
(45) Date of Patent: May 9, 2006

(54) PROCESS FOR PRODUCING PURIFIED (METH)ACRYLIC ACID

(75) Inventors: Shuhei Yada, Mie-ken (JP); Kenji Takasaki, Mie-ken (JP); Yasushi Ogawa, Mie-ken (JP); Yoshiro Suzuki, Mie-ken (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 11/019,649

(22) Filed: Dec. 23, 2004

(65) Prior Publication Data

US 2005/0187405 A1    Aug. 25, 2005

Related U.S. Application Data

(63) Continuation of application No. PCT/JP2004/15367, filed on Oct. 18, 2004.

(30) Foreign Application Priority Data

Nov. 11, 2003   (JP) .............................. 2003-380582

(51) Int. Cl.
*C07C 51/42*   (2006.01)
(52) U.S. Cl. ..................................... 562/600
(58) Field of Classification Search .................... None
See application file for complete search history.

(56) References Cited

U.S. PATENT DOCUMENTS 5,759,358 A * 6/1998 Bauer, Jr. et al. ............. 203/38

* cited by examiner

*Primary Examiner*—Paul A. Zucker
(74) *Attorney, Agent, or Firm*—Nixon & Vanderhye P.C.

(57) ABSTRACT

The present invention provides a process for producing purified (meth)acrylic acid by subjecting crude (meth) acrylic acid containing maleic acids and aldehydes as impurities to distillation, the said process comprising, prior to the distillation, the following steps:

(A) adding hydrazines to the crude (meth)acrylic acid at a temperature of not less than a melting point of acrylic acid and not more than 50° C. to react the maleic acids with the hydrazines;

(B) heat-treating the reaction solution obtained in the above step (A) at a temperature of 60 to 90° C. to convert the reaction product into a substance soluble in the reaction solution; and (C) adding hydrazines to the thus heat-treated reaction solution obtained in the above step (B) at a temperature of not less than the melting point of acrylic acid and not more than 50° C. to react the aldehydes with the hydrazines, thereby producing a substance soluble in the reaction solution.

In the process for producing purified (meth)acrylic acid from the crude (meth)acrylic acid containing maleic acids and aldehydes as impurities according to the present invention, not only the maleic acids but also the aldehydes can be removed therefrom to a sufficient extent, and the operation thereof can be continued for a long period of time.

4 Claims, No Drawings

PROCESS FOR PRODUCING PURIFIED (METH)ACRYLIC ACID

This application is a continuation of international application PCT/JP2004/15367 filed Oct. 18, 2004 which claims benefit of Japanese Application No. 2003-380582 filed Nov. 11, 2003, the entire content of which is hereby incorporated by reference.

TECHNICAL FIELD

The present invention relates to a process for producing purified (meth)acrylic acid, and more particularly, to a process for producing high-purity (meth)acrylic acid by subjecting crude (meth)acrylic acid containing maleic acids and aldehydes as impurities, which is obtained by gas-phase catalytic oxidation, to distillation. Meanwhile, the "(meth) acrylic acid" described in the present specification generally includes acrylic acid and methacrylic acid.

BACKGROUND ARTS

In the process for producing (meth)acrylic acid by gas-phase catalytic oxidation, maleic acids such as maleic acid and maleic anhydride, aldehydes such as furfural and benzaldehyde, etc., are by-produced. In addition, carboxylic acids such as acetic acid, water, etc., are also by-produced. In the case where the (meth)acrylic acid containing such impurities is used as a raw material for production of polymers thereof, there tend to arise problems such as delayed polymerization reaction, low polymerization degree and discoloration of the resultant polymers. Therefore, it has been demanded to provide high-purity (meth)acrylic acid, in particular, usable as a raw material of high-absorption resin products such as paper diapers, food additives, etc.

As the process for producing purified (meth)acrylic acid from the above crude (meth)acrylic acid by a distillation method, there is known such a process including, prior to the distillation step, the step (A) of adding hydrazines to the crude (meth)acrylic acid at a temperature of not less than a melting point of acrylic acid and not more than 50° C. to obtain a reaction product of the maleic acids and the hydrazines; and the step (B) of heat-treating the reaction solution obtained in the step (A) at a temperature of not less than 60 and less than 80° C. (Japanese Patent Application Laid-open (KOKAI) No. 2003-206257). The step (A) is a step of converting the maleic acids and aldehydes into high-boiling substances, whereas the step (B) is a step of converting the reaction products of the maleic acids and the hydrazines into soluble substances. Meanwhile, the reaction products of the maleic acids and the hydrazines, which are obtained in the step (A) are soluble substances.

However, in fact, the above conventional process has failed to remove the aldehydes as impurities from the crude (meth)acrylic acid to a sufficient extent. According to the present inventors' knowledge, the reason therefor is considered to be that the reaction products of the maleic acids and the hydrazines are decomposed in the step (B) so that the aldehydes are reproduced.

DISCLOSURE OF THE INVENTION

Problem to be Solved by the Invention

The present invention has been made for solving the above conventional problems. An object of the present invention is to provide a process for producing purified (meth)acrylic acid from crude (meth)acrylic acid containing maleic acids and aldehydes as impurities, which is capable of removing not only the maleic acids but also the aldehydes from the crude (meth)acrylic acid to a sufficient extent, is prevented from suffering from formation of sludge, and enables a stable continuous operation thereof for a long period of time.

Method for Solving the Problem

The present invention has been attained on the basis of the above finding. To accomplish the aim, in an aspect of the present invention, there is provided a process for producing purified (meth)acrylic acid by subjecting crude (meth) acrylic acid containing maleic acids and aldehydes as impurities to distillation, the said process comprising, prior to the distillation, the following steps:

(A) adding hydrazines to the crude (meth)acrylic acid at a temperature of not less than a melting point of acrylic acid and not more than 50° C. to react the maleic acids with the hydrazines;

(B) heat-treating the reaction solution obtained in the above step (A) at a temperature of 60 to 90° C. to convert the reaction product into a substance soluble in the reaction solution; and (C) adding hydrazines to the thus heat-treated reaction solution obtained in the above step (B) at a temperature of not less than the melting point of acrylic acid and not more than 50° C. to react the aldehydes with the hydrazines, thereby producing a substance soluble in the reaction solution.

Effect of the Invention

Thus, according to the present invention, high-purity (meth)acrylic acid having an extremely small content of impurities can be produced in economical manner by efficiently removing the impurities from crude (meth)acrylic acid containing maleic acids and aldehydes as the impurities, which is obtained by gas-phase catalytic oxidation. Therefore, the present invention has a considerably large industrial value.

PREFERRED EMBODIMENT FOR CARRYING OUT THE INVENTION

The present invention is described in detail below. First, the general process for producing (meth)acrylic acid is explained. For example, the crude acrylic acid may be produced by successively conducting the following steps (1) to (5):

(1) Step of forming an acrylic acid-containing gas by an one-stage oxidation method in which acrylic acid is directly produced by reacting propane, propylene and/or acrolein with a molecular oxygen-containing gas in the presence of a molybdenum oxide-based solid oxidation catalyst, etc.; or a two-stage oxidation method in which propylene is first reacted with a molecular oxygen-containing gas in the presence of a molybdenum oxide-based solid oxidation catalyst, etc., in the first reaction zone to produce acrolein, and then the resultant acrolein is reacted with a molecular oxygen in the presence of the molybdenum oxide-based solid oxidation catalyst, etc., in the second reaction zone to produce acrylic acid.

(2) Step of bringing the thus obtained acrylic acid-containing gas into a counter-flow contact with water in an absorption column to produce an aqueous solution of crude acrylic acid.

(3) Step of extracting the resultant aqueous solution of crude acrylic acid with an organic solvent such as, for example, methyl isobutyl ketone and diisobutyl ketone, and then distilling the resultant extract to obtain an acrylic acid-containing liquid as a bottom fraction; or subjecting the resultant aqueous solution of crude acrylic acid together with an azeotropic agent such as toluene, butyl acetate and octane to azeotropic dehydration, for example, at a temperature of 80 to 100° C. under a pressure of 6.67 to 20 kPa to obtain an acrylic acid-containing liquid as a bottom fraction.

(4) Step of subjecting the thus obtained acrylic acid-containing liquid to distillation treatment to remove low-boiling components such as acetic acid therefrom, and then further subjecting the resultant bottom liquid to distillation treatment to obtain crude acrylic acid as a top fraction as well as high-boiling substances including an acrylic acid dimer as a bottom liquid.

(5) Step of further subjecting the acrylic acid dimer obtained as the bottom liquid to distillation treatment to obtain crude acrylic acid as a top fraction.

The detailed explanation of the process for production of methacrylic acid is omitted here. However, the methacrylic acid may be produced, for example, by contacting a reaction gas produced from a raw material such as isobutylene by a gas-phase catalytic oxidation method, with water to obtain a methacrylic acid-containing solution by the same method as used in the above process for production of acrylic acid, and then subjecting the thus obtained reaction solution to a methacrylic acid recovery step to obtain the methacrylic acid as a bottom fraction. In the process for production of any of acrylic acid and methacrylic acid, since the maleic acids and aldehydes contained as impurities have a boiling point close to that of the (meth)acrylic acid, i.e., similar properties to those of the (meth)acrylic acid, the above extraction and distillation treatments have failed to sufficiently separate the impurities from the aimed reaction product, so that the impurities are entrained thereon.

According to the present invention, in the process for producing purified (meth)acrylic acid by subjecting the crude (meth)acrylic acid containing maleic acids and aldehydes as impurities, which is obtained by the above method, to distillation, the following steps (A) to (C) (pre-distillation treatment steps) are successively conducted prior to the distillation step.

(A) Step of adding hydrazines to the crude (meth)acrylic acid at a temperature of not less than a melting point of acrylic acid and not more than 50° C. to react the maleic acids with the hydrazines;

(B) Step of heat-treating the reaction solution obtained in the above step (A) at a temperature of 60 to 90° C. to convert the reaction product into a substance soluble in the reaction solution; and (C) Step of adding hydrazines to the thus heat-treated reaction solution obtained in the step (B) at a temperature of not less than the melting point of acrylic acid and not more than 50° C. to react the aldehydes with the hydrazines, thereby producing a substance soluble in the reaction solution.

The concentration of the maleic acids contained in the crude (meth)acrylic acid used as a raw material in the pre-distillation treatment steps is usually 2,000 to 10,000 ppm, preferably 2,000 to 5,000 ppm. In order to reduce the concentration of the maleic acids in the crude (meth)acrylic acid to less than 2,000 ppm, a large load tends to be required upon conducting such a purification step. On the other hand, when the concentration of the maleic acids in the crude (meth)acrylic acid is more than 10,000 ppm, the amount of the hydrazines consumed tends to become too large and as a result, the purification treatment tends to become uneconomical. Therefore, in the present invention, although the (meth)acrylic acid-containing solution obtained in the above step (3) may be used as the raw material, from the above viewpoints, the crude (meth)acrylic acids obtained in the steps (4) and (5) are usually used as the raw material.

In the step (A), the hydrazines are added to the crude (meth)acrylic acid to produce a reaction product of the maleic acids and the hydrazines. Examples of the hydrazines may include hydrazine, hydrazine hydrate and mixtures thereof. Examples of the maleic acids may include maleic acid, maleic anhydride and citraconic acid. Also, the reaction apparatus used in the process of the present invention is not particularly restricted as long as the temperature and reaction time required in the process can be ensured. Examples of the suitable reaction apparatus may include reaction vessels with a stirrer and tube-type reaction vessels.

The temperature used in the reaction between the maleic acids and the hydrazines is not less than a melting point of acrylic acid and not more than 50° C., preferably 15 to 40° C., and the reaction time is usually not less than 10 min, preferably 30 min to 3 hr. When the reaction temperature is less than the melting point of acrylic acid, the rate of the reaction between the maleic acids and the hydrazines tends to become low. On the other hand, when the reaction temperature is more than 50° C., the hydrazines tends to be undesirably decomposed.

The amount of the hydrazines added is usually 0.1 to 5 moles, preferably 0.5 to 3 moles based on one mole of a total amount of the maleic acids and the aldehydes contained in the crude (meth)acrylic acid. When the amount of the hydrazines added is less than 0.1 mole, the reaction between the maleic acids and the hydrazines tends to become insufficient. On the other hand, when the amount of the hydrazines added is more than 5 moles, the use of such a large amount of the hydrazines tends to become uneconomical.

In the step (A), although the hydrazines are mainly reacted with the maleic acids, a small amount of the maleic acids might remain unreacted in some cases. Meanwhile, it is presumed that the reaction product of the hydrazines and the maleic acids is maleic monohydrazides.

In the step (B), the reaction solution obtained in the step (A) is subjected to heat treatment. With this procedure, the above reaction product is converted into a substance soluble in the reaction solution. The heat-treating apparatus is not particularly restricted as long as an inside temperature of the apparatus can be controlled to the above temperature range. As such an apparatus, there may be suitably used, for example, heat exchangers.

The heat-treating temperature is in the range of 60 to 90° C., preferably 62 to 80° C., and the heat-treating time is usually not less than 10 min, preferably 30 min to 3 hr. When the heat-treating temperature is less than 60° C., the reaction product of the maleic acids and the hydrazines may fail to be sufficiently converted into the soluble substance, resulting in precipitation of the reaction product as well as formation of sludge. On the other hand, when the heat-treating temperature is more than 90° C., the acrylic acid tends to be undesirably polymerized.

In the step (C), hydrazines are added to the thus heat-treated reaction solution obtained in the step (B) to produce a reaction product of the aldehydes and the hydrazines. Meanwhile, it is presumed that the reaction product of the aldehydes and the hydrazines is hydrazone compounds. As the hydrazines, there may be used the same compounds as used in the step (A). Examples of the aldehydes may include furfural and benzaldehyde. Examples of the hydrazone compounds may include furfural hydrazone and benzaldehyde hydrazone. In addition, as the reaction apparatus for conducting the step (C), there may also be used the same apparatus as used in the step (A).

The temperature used in the reaction between the aldehydes and the hydrazines is not less than the melting point of acrylic acid and not more than 50° C., preferably 15 to 35° C., and the reaction time is usually not less than 10 min, preferably 30 min to 3 hr. When the reaction temperature is less than the melting point of acrylic acid, the rate of the reaction between the aldehydes and the hydrazines tends to become low. On the other hand, when the reaction temperature is more than 50° C., the hydrazines tend to be undesirably decomposed.

Meanwhile, a cooling apparatus used for controlling the heat-treated reaction solution obtained by the step (B) to the temperature of not less than the melting point of acrylic acid and not more than 50° C. is not particularly restricted, as long as the apparatus is capable of setting and controlling an inside temperature thereof to the above temperature range. Examples of the suitable cooling apparatus may include a refrigerator.

The amount of the hydrazines added is usually 0.1 to 5 moles, preferably 0.5 to 3 moles based on one mole of a total amount of the maleic acids and the aldehydes contained in the crude acrylic acid obtained at a discharging port of the step (B). When the amount of the hydrazines added is less than 0.1 mole, the reaction between the maleic acid and the hydrazines or between the aldehydes and the hydrazines tends to become insufficient. On the other hand, when the amount of the hydrazines added is more than 5 moles, the use of such a large amount of the hydrazines tends to be uneconomical.

Next, the crude (meth)acrylic acid produced by successively conducting the above steps (A) to (C) is subjected to distillation by known methods to produce high-purity (meth) acrylic acid. Meanwhile, the "high-purity" used herein means that the contents of the maleic acids, furfural and benzaldehyde in the thus purified (meth)acrylic acid is less than 30 ppm, less than 3 ppm and less than 10 ppm, respectively. The operating conditions of the distillation column may vary depending upon composition of raw materials to be distilled, recovery rate, purity of (meth) acrylic acid as a distillate, etc. However, since the (meth) acrylic acid is an easily-polymerizable compound, the distillation temperature and pressure are preferably controlled as low as possible. More specifically, the bottom temperature is usually 60 to 100° C., and the top pressure is usually 1.33 to 26.7 kPa.

Upon the distillation, conventional polymerization inhibitors may be used. Examples of the polymerization inhibitors may include N-oxyl compounds such as tert-butyl nitroxide, 2,2,6,6-tetramethyl-4-hydroxypiperidyl-1-oxyl, 2,2,6,6-tetramethylpiperidyl-1-oxyl, 2,2,6,6-tetramethylpiperidino-oxyl, 4-hydroxy-2,2,6,6-tetramethylpiperidino-oxyl and 4,4',4"-tris-1-(2,2,6,6-tetramethylpiperidino-oxyl)phosphite; phenol compounds such as hydroquinone, methoquinone, pyrogallol, catechol and resorcin; phenothiazine compounds such as phenothiazine, bis-(α-methylbenzyl) phenothiazine, 3,7-dioctyl phenothiazine and bis-(α-dimethylbenzyl)phenothiazine; and copper compounds such as cupric chloride, copper acetate, copper carbonate, copper acrylate, copper dimethyldithiocarbamate, copper diethyldithiocarbamate and copper dibutyldithiocarbamate. These polymerization inhibitors may be used in the combination of any two or more thereof. The polymerization inhibitor is usually added in an amount of 1 to 1,000 ppm based on the crude (meth)acrylic acid.

As the distillation method, there may be used various methods such as simple distillation and precision distillation. The distillation treatment may be conducted by either a batch method or a continuous method. Of these methods, the continuous method is preferred from the industrial viewpoint. Also, as the distillation apparatus, there may be used conventionally known apparatuses.

In the distillation column, there may be used trays or packing materials. Examples of the commercially available regular packing materials may include "SULZER PACKING" produced by Sulzer Brothers Limited, "SUMITOMO SULZER PACKING" produced by Sumitomo Heavy Industries Ltd., "MELAPACK" produced by Sumitomo Heavy Industries Ltd., "JEMPACK" produced by Grich Inc., "MONTZPACK" produced by Montz Inc., "GOODROLL PACKING" produced by Tokyo Special Wire Netting Co. Ltd., "HONEYCOMB PACK" produced NGK INSULATORS, LTD., and "IMPULSE PACKING" produced NAGAOKA Corporation. Examples of the commercially available irregular packing materials may include "INTERLOCKS SADDLE" produced by Norton Inc., "TERALET" produced by Nittetu Chemical Engineering Ltd., "POLE RING" both produced by BASF AG, "CASCADE MINI-RING" produced by Mass-Transfer Inc., and "FLEXI-RING" produced by JGC CORPORATION. As the suitable combination of the packing materials and the trays, there may be used the combination of the regular packing materials and the trays, and the combination of the irregular packing materials and the trays.

Meanwhile, examples of the trays may include trays having a downcomer such as a bubble-cap tray, a perforated plate tray, a bubble tray, a super-flux tray and a max-flux tray, and trays having no downcomer such as a dual-flow tray.

EXAMPLES

The present invention is described in more detail by Example, but the Example is only illustrative and not intended to limit the scope of the present invention. Meanwhile, in the following Example and Comparative Example, the analysis of the respective compositions was conducted by gas chromatography. However, since maleic acid is converted into maleic anhydride during the gas chromatographic analysis, the total content of the maleic acid and maleic anhydride was regarded as the content of maleic acid. Meanwhile, in the following Example and Comparative Example, "ppm" means "ppm by weight".

Example 1

In this Example, as the raw material, there was used the crude acrylic acid obtained in the above step (4) by gas-phase catalytic oxidation method, which contained as main impurities 3,470 ppm of maleic acids, 267 ppm of furfural and 322 ppm of benzaldehyde.

In the step (A), a hydrazine hydrate (2,100 ppm) was added in a molar amount equivalent to total moles of the maleic acids and the aldehydes contained in the crude acrylic acid, and the obtained mixture was flowed through a tube-type reactor at a whole liquid flow rate of 5,000 kg/hr and a temperature of 20° C. for a residence time of 2 hours.

Successively, in the step (B), the thus obtained reaction solution was heated to 65° C. using a heat exchanger. After completion of the heating, when the obtained solution was visually observed, it was confirmed that no solid reaction product of the maleic acids and the hydrazines as produced in the step (A) was present in the solution obtained in the step (B). As a result of subjecting the obtained reaction solution to composition analysis, it was confirmed that the contents of the maleic acids, furfural and benzaldehyde in the solution were 994 ppm, 5.6 ppm and 45.4 ppm, respectively.

Then, in the step (C), the thus obtained solution was cooled to 20° C. using a cooler, and then a hydrazine hydrate (540 ppm) was added thereto in a molar amount equivalent to total moles of the maleic acids and the aldehydes. The thus obtained mixture was flowed through a tube-type reactor at a temperature of 20° C. for a residence time of 2 hours. As a result of subjecting the obtained solution to composition analysis, it was confirmed that the contents of the maleic acids, furfural and benzaldehyde in the solution were 298 ppm, less than 1.0 ppm and less than 1.0 ppm, respectively.

Next, the thus obtained reaction solution was fed to a distillation column and subjected to continuous distillation. More specifically, 99% by weight of the solution fed was continuously distilled out at a bottom temperature of 74° C., and a part of the thus obtained distillate was introduced as a refluxing solution at a reflux ratio of 1.0 into the distillation column from a top thereof. Meanwhile, upon the distillation, methoquinone (as a polymerization inhibitor) was dissolved in the refluxing solution in an amount corresponding to 10 ppm based on the amount of the liquid introduced into the distillation column, and the resultant solution was introduced into the distillation column.

As a result, it was confirmed that the amount of any of the maleic acids, furfural and benzaldehyde contained in the purified acrylic acid obtained as a distillate from the top of the distillation column was less than 1 ppm, and the distillation procedure was stably continued for 10 months under this condition.

Comparative Example 1

The same procedure as defined in Example 1 was conducted except that no step (C) was conducted. The obtained reaction solution prior to feeding it to the distillation column was subjected to composition analysis by gas chromatography. As a result, it was confirmed that the contents of the maleic acids, furfural and benzaldehyde in the solution were 1,006 ppm, 6.0 ppm and 50.0 ppm, respectively. Further, after subjecting the solution to the continuous distillation procedure, it was confirmed that the contents of the maleic acids, furfural and benzaldehyde in the purified acrylic acid obtained as a distillate from the top of the distillation column was 188 ppm, 5.6 ppm and 15 ppm, respectively. Therefore, the thus obtained acrylic acid did not belong to the high-purity acrylic acid as defined in the present invention.

The invention claimed is:

1. A process for producing purified (meth)acrylic acid by subjecting crude (meth)acrylic acid containing maleic acids and aldehydes as impurities to distillation, said process comprising, prior to the distillation, the following steps:
   (A) adding hydrazines to the crude (meth)acrylic acid at a temperature of not less than a melting point of acrylic acid and not more than 50° C. to obtain a reaction solution containing a reaction product of the maleic acids and the hydrazines;
   (B) heat-treating the reaction solution obtained in the above step (A) at a temperature of 60 to 90° C. to convert the reaction product into a soluble substance; and
   (C) adding hydrazines to the thus heat-treated reaction solution obtained in the above step (B) at a temperature of not less than the melting point of acrylic acid and not more than 50° C. to obtain a soluble reaction product of the aldehydes and the hydrazines.

2. A process according to claim 1, wherein the reaction of the step (A) is conducted at a temperature of 15 to 40° C. for 30 minutes to 3 hours, and the amount of the hydrazines added in the step (A) is 0.1 to 5 moles based on one mole of a total amount of the maleic acids and the aldehydes contained in the crude (meth)acrylic acid.

3. A process according to claim 1, wherein the heat treatment of the step (B) is conducted at a temperature of 62 to 80° C. for 30 minutes to 3 hours.

4. A process according to claim 1, wherein the reaction of the step (C) is conducted at a temperature of 15 to 35° C. for 30 minutes to 3 hours, and the amount of the hydrazines added in the step (C) is 0.1 to 5 moles based on one mole of a total amount of the maleic acids and the aldehydes contained in the crude (meth)acrylic acid as an effluent obtained at an outlet of the step (B).

* * * * *